United States Patent [19]
Devens

[11] Patent Number: 5,401,235
[45] Date of Patent: Mar. 28, 1995

[54] DYNAMIC VARIABLE TORQUE LONG BONE TORSION REDUCER

[76] Inventor: Mark F. Devens, 659 Arlington Pl., Chicago, Ill. 60614

[21] Appl. No.: 259,246

[22] Filed: Jun. 13, 1994

Related U.S. Application Data

[62] Division of Ser. No. 893,174, Jun. 3, 1992, Pat. No. 5,346,463.

[51] Int. Cl.⁶ .............................................. A61F 5/00
[52] U.S. Cl. ...................................... 602/23; 602/24
[58] Field of Search .................. 36/142, 143, 144, 158, 36/168; 602/23, 24, 28; 128/882

[56] References Cited

U.S. PATENT DOCUMENTS

| | | | |
|---|---|---|---|
| 2,906,261 | 9/1959 | Craig | 602/24 |
| 2,920,620 | 1/1960 | Rogers | 602/28 |
| 3,304,937 | 2/1967 | Callender | 602/28 |
| 3,487,829 | 1/1990 | Barnett | 602/24 |
| 3,892,231 | 7/1975 | Tummillo | 602/24 |
| 3,931,817 | 1/1976 | Infanca | 602/24 |
| 3,958,567 | 5/1976 | Callender | 602/24 |
| 4,249,523 | 2/1981 | Bidwell | 602/24 |

*Primary Examiner*—Michael A. Brown
*Attorney, Agent, or Firm*—Jon Carl Gealow

[57] ABSTRACT

An orthopedic appliance which when attached to the distal ends of the extremities of a user, applies a dynamic corrective torque or force to the long bones of those extremities. A pair of torque applying members, each of which is attached to a distal end of one of the pair of long bones, are supported for rotation on an elongated spacing member, a pair of dynamic force applying members create a torque between each of the torque applying members and the elongated spacing member.

17 Claims, 5 Drawing Sheets

DYNAMIC VARIABLE TORQUE LONG BONE TORSION REDUCER

This application is a division of U.S. application Ser. No. 07/893,174, filed Jun. 3, 1992, now U.S. Pat. No. 5,346,463.

BACKGROUND OF THE INVENTION

1. Field of the Invention

This invention relates in general to non-invasive external braces for the human limbs (Orthotics) and in particular, to a device for the treatment of torsional deformities of the lower limbs.

2. Description of Related Art Including Information Disclosed under Secs. 1.97-1.99

Torsional deformities of long bones have been described in medical literature for many years. Various devices have been used in the past which are claimed to reduce or reverse these deformities.

In the past few years, a controversy has arisen over whether any of the current devices actually affect a reduction or correction. Some have advanced the proposition that there is a natural tendency toward the gradual correction of these deformities as the child grows, even without the assistance of currently available devices. That is, it is thought that most torsional deformities will correct over time without treatment, such that the application of the currently available devices have merely appeared successful due to the natural correction. The deformities which were treated, but which did not respond to treatment, were considered to be "extreme" such as to require invasive intervention (surgery).

There are a number of currently available devices, which through various types of construction all perform the same function. Even with improvements, the current devices all lack an ingredient or feature which is essential to be truly effective in correcting torsional deformities. That is, the continuing application of a dynamic torque or force to the long bones.

The so-called Dennis-Browne type Bar, provided by numerous manufacturers, has been used for decades in the correction of torsional deformities of the lower limbs. This device includes a bar at the ends of which are fastened two plates, each of which plates is secured to a shoe. The plates are secured to the bar so as to hold the shoes in a predetermined angular position with respect to each other, so as to rotate and maintain the long bones in a position opposite the direction of the torsional deformity. Being a static device, it does not dynamically affect correction, but simply resists further deformation. A recent paper by Morey S. Moreland, M.D., entitled: *Dennis Browne Splint-Torsion or No Torsion*, has reported that when a user is sleeping (the period during which the bar is customarily used), there is virtually no corrective force applied to the extremities of the long bones. See Paper No. 31, page 39.

An improvement on the Dennis-Brown Bar provides a mechanism linking the shoes which permits a user to independently kick and move each foot, while at the same time keeping the extremities in the desired rotation with respect to each other. Nevertheless, it is still a static device, such that once the rotation is set there is no further force applied to the long bones. Thus, this device simply resists further deformity as does the Dennis-Brown Bar.

Another system keeps the wearer's knee flexed at a right angle, so as to isolate the area of treatment to the tibia. Again, a shoe is mounted on a plate whereby the wearer's extremity may be rotated in a direction opposite the deformity. This device has the ability to isolate the legs from each other, but again this device simply resists further deformity, it does not apply a dynamic correcting force.

Still another system uses cables which are attached to a pelvic band and to the wearer's shoes, such that the cables maintain the shoes in a predetermined position like the above-mentioned devices. Again, since the system is set to keep the extremity rotated opposite the deformity, once it is set it applies no more force to the extremity, it simply resists further deformation.

Whatever the merits, features and advantages of the above-cited devices, none of them achieve or fulfill the purposes of the applicants dynamic variable tension long bone torsion reducer.

SUMMARY OF THE INVENTION

The object of the applicant's invention is to correct torsional deformities by causing a continuous force to be applied to the deformity in a direction opposite the deformity. The applicant's orthopedic appliance for applying a continuous corrective force, such as provided by a torsion spring, will initially apply a force of a greater magnitude, which force will diminish as the desired correction is achieved. The applicant's appliance may also include means for adjusting the force as well as the ability to adjust the rotational position at which the force dissipates. Use of the applicant's orthopedic appliance results in the proper application of the adjustable dynamic force needed for the correction of a long bone torsional deformity.

Accordingly, it is an object of this invention to correct torsional deformities of the long bones by the proper application of an adjustable dynamic force. It is a further object of this invention to provide an orthopedic appliance which will apply the proper, adjustable dynamic force to the extremities of the long bones of a patient to correct a long bone torsional deformity. Further, it is desirable to provide an orthopedic appliance which is readily manufactured and easily applied and adjusted to a patient's needs for the correction of a long bone torsional deformity.

In accordance with this invention, an orthopedic appliance is provided which may be readily applied to a patient for the correction of a long bone torsional deformity. In a preferred embodiment of the orthopedic appliance of the applicant's invention, a pair of torque applying members are rotationally supported, one at each end of an elongated spacing member. A pair of torsion springs are provided to exert a torque between each of the torque applying members and the spacing member. Suitable for use as torsion springs are wound coil springs and clock type springs. One end of each of the torsion springs is secured to the spacing member while the other is secured to the torque applying member. The torsion springs are adjustably secured to either or both the torque applying member and the spacing member, such that the amount of torque, and the angle at which the torque is applied to the long bone, may be adjusted. In another embodiment of the applicants invention, the spacing member, as a support for the torque applying member, is replaced by a Z-shaped member, having a central portion and a pair of ends, each of which is perpendicular to the central portion and which extend in opposite directions from the central member. One of the ends is secured to the patients leg above the knee, the central member extending along the back of the lower leg, and the other end extends under the patient's foot to support the torque applying member.

DETAILED DESCRIPTION OF THE PREFERRED EMBODIMENTS

Figure 1:
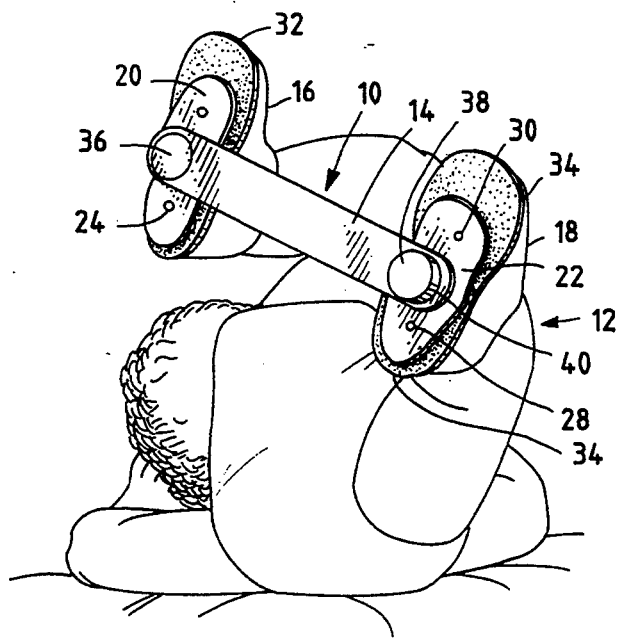
FIG. 1 is a perspective view of a first embodiment of the orthopedic appliance of this invention applied to a child's lower leg extremities.

Referring to FIG. 1, a preferred embodiment of the orthopedic appliance 10 of this invention is shown applied to the lower extremities of a child 12. The orthopedic appliance 10 of this invention includes an elongated spacing member or bar 14 which extends between the lower surface of the feet 16 and 18 of the child. Pivotally mounted on the bar 14 are first and second torque applying members or foot plates 20 and 22. The plates 20 and 22 are secured by fastening means such as screws or rivets (not shown) which are received in holes 24, 26, 28 and 30 to the soles 32 and 34 of shoes which are placed on the child's feet 16 and 18 respectively.

The plate 20 is pivotally mounted on the bar 14 by a pivotal support member such as is represented by the head 36 of a pivotal support pin. The plate 22 is pivotally supported on the bar 14, by a pivotal support mechanism 38. The pivotally support mechanism 38 contains a torque applying assembly 40, which applies a torque between the bar 14 and the plate 22. This torque is in turn applied between the feet 16 and 18 of the child 12 to cause the feet, and therefore the legs, to be rotated with respect to each other. The orthopedic appliance can be assembled such that the rotational force of the torque applying member 40 can cause the toes of the feet 16 and 18 to be rotated either toward or apart from each other, depending upon the needs of the child to which the orthopedic appliance is applied.

Figure 2:
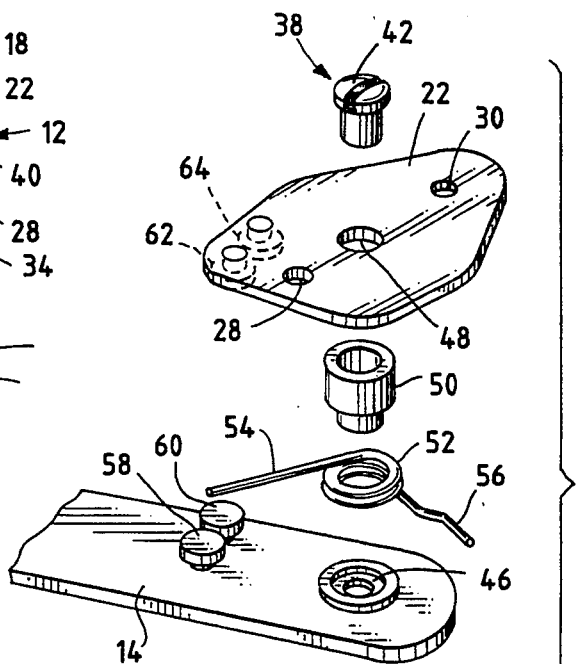
FIG. 2 is an exploded partial view of a second embodiment of the orthopedic appliance of this invention.
Figure 3:
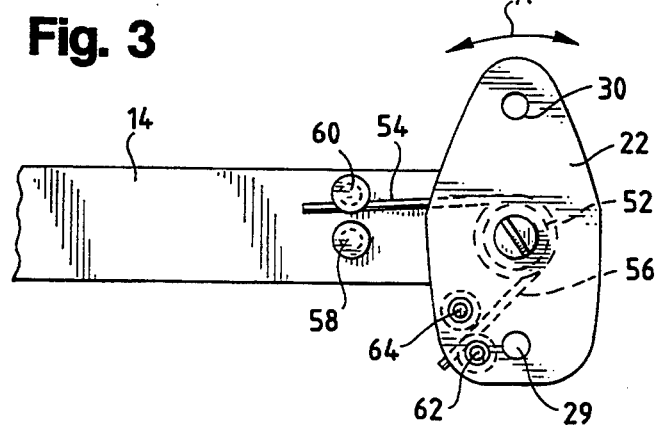
FIG. 3 is a top plan view of a portion of the second embodiment of the orthopedic appliance of this invention.

The construction of the first embodiment of the orthopedic appliance of this invention being somewhat more complex, the second embodiment will first be described in detail by making reference to FIGS. 2, 3 and 4. Components of the second embodiment which are similar to components for the first embodiment will be identified with the same reference numerals. The torque applying plate 22 is pivotally supported on the bar 14 by a pivotally supported mechanism 38 which includes an internally threaded member 42 and an externally threaded member 44, both of which pass through apertures 46 and 48 in bar 14 and plate 22 respectively. The externally threaded member 44 and the internally threaded member 42 are secured to each other.

A cylindrical spacer 50 surrounds the internally threaded member 42 to maintain a spacing between the plate 22 and the bar 14. Placed around the spacer 50 is a coil spring 52 having two projecting ends 54 and 56. Two pairs of pins or abutments 58 and 60, and 62 and 64 are secured to the facing surfaces of bar 14 and plate 22 respectively for engaging the ends of the spring 52. As shown in FIG. 3, end 54 of spring 52 is placed in engagement with pin 60, and end 56 is placed in engagement with pin 62. With the ends of the spring so engaged, a counter clock-wise force, as shown by the arrow A, is applied to the plate 22 with respect to the bar 14. The ends 54 and 56 of spring 52 are shown closer together in FIG. 3, than in their natural state in FIG. 2. For the plate 22 to be maintained in the position shown in FIG. 3 with respect to bar 14, a force in the clockwise direction must be applied to the plate 22 by the legs of the child 12 fitted with the appliance.

In accordance with this invention, it is desirable that a dynamic force be continually applied to the extremities of the user when the appliance is in use. Thus, as the relative natural positions of the extremities of the limbs are corrected, it is necessary to readjust the relative positions of the plate 22 and bar 14 at which the torque is applied, and possibly to increase the torque applied between the bar 14 and the plate 22 to provide additional correction. As shown in FIG. 3, this additional force can be provided by positioning spring end 54 against pin 58, rather than pin 60. The torque may be still further increased by positioning the spring end 56 against the pin 64, rather than pin 62.

While only two pins are shown in bar 14 and plate 22, additional pins may be provided such that further adjustment of the torque is provided. Further, by choosing various pairs of pins to engage the ends 54 and 56 of the spring 52, the relative angle of the plate 22, with respect to the bar 14, at which the torque is applied may be adjusted. Further, the torque applied to the user could also be adjusted by changing the spring such that more or less torque would be applied by either choosing a heavier or a lighter spring, or a spring whose natural or at rest position has its ends 54 and 56 closer or farther apart.

Figure 4:
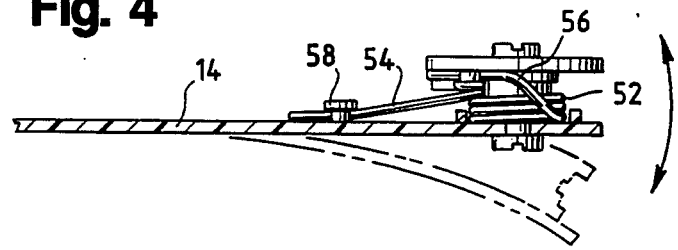
FIG. 4 is a side view of a second embodiment of the orthopedic appliance of this invention.

As shown in FIG. 4, the bar 14 is flexible such that some movement with respect to each other of the extremities of the user of the appliance are permitted.

Figure 5:
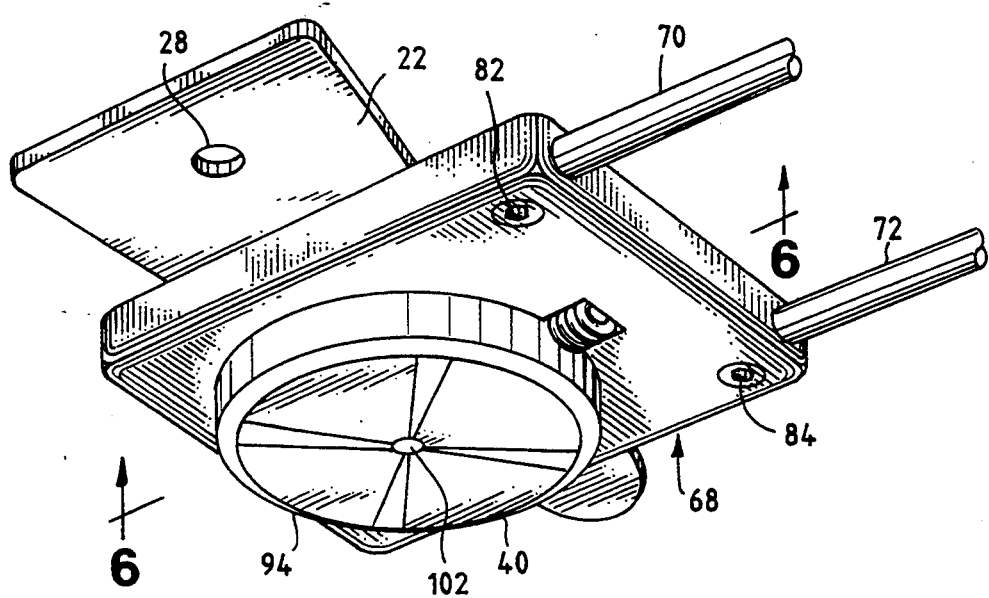
FIG. 5 is a perspective view of a portion of the orthopedic appliance of the first embodiment of this invention.
Figure 6:
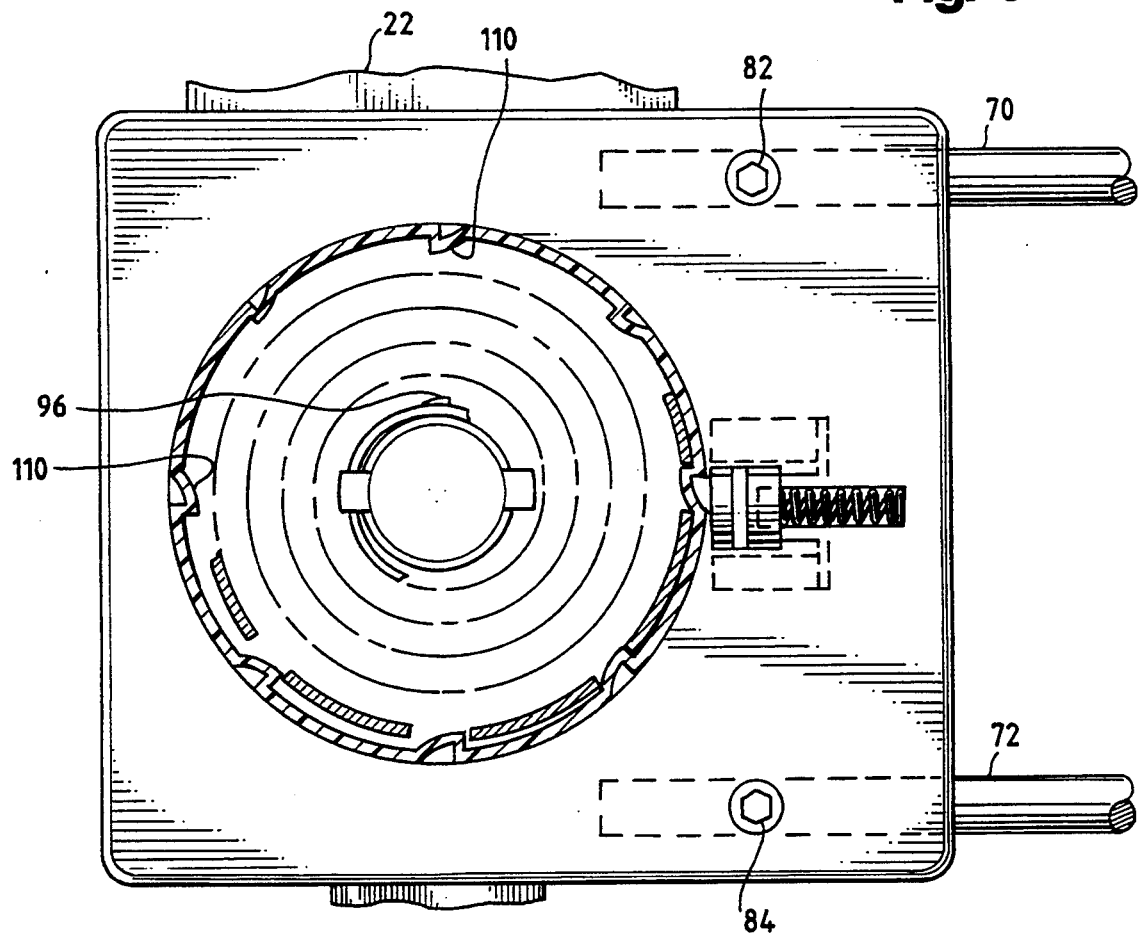
FIG. 6 is a bottom view of a portion of the orthopedic appliance of the first embodiment of this invention.
Figure 7:
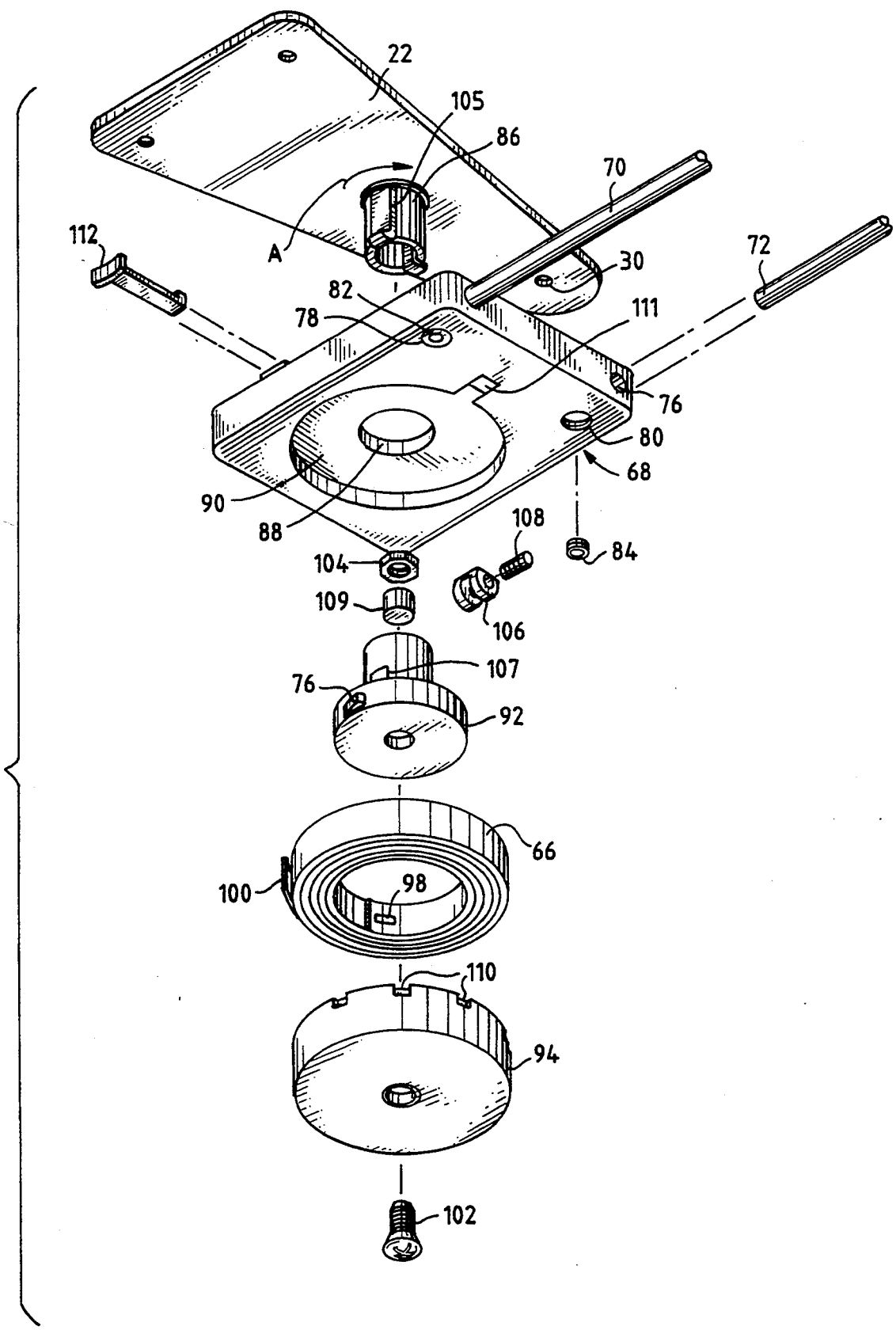
FIG. 7 is an exploded view of a portion of the orthopedic appliance of the first embodiment of this invention.

The first embodiment of the applicant's invention as shown in FIG. 1 is further illustrated in FIGS. 5, 6 and 7. While in FIG. 1, the bar 14 is shown as a solid member, in FIGS. 5, 6 and 7, it is formed of main body housings 68, one of which is shown in FIG. 7, and a pair of connecting rods 70 and 72 extending between the housings. The ends of the rods 70 and 72 are received in apertures 74 and 76 formed in the main body housing 68 and are positioned to provide the desired spacing between the feet of the user. Threaded apertures 78 and 80 intersect the apertures 74 and 76 and receive set screws 82 and 84, the ends of which engage the rods 70 and 72 to secure them in the apertures 74 and 76. The torque applying foot plate 22 is provided with a generally cylindrical projection 86 which passes through a hole 88 formed in the housing 68. A cylindrical recess 90 is provided in the housing 68 surrounding the hole 88 for receiving a clock or coil spring 66, a spool 92 around which the clock spring is wound, and a cylindrical cover 94 which surrounds the outer periphery of the clock spring.

The outer periphery of the spool 92 is provided with a protrusion or detent 96 which engages a slot or notch 98 in the inside end of the clock spring 66 to secure the inside end of the clock spring to the spool 92. A similar detent (not shown) is provided on the inside surface of the cylindrical cover 94 to engage a notch 100 in the outer end of the clock spring 66 to secure the outer end of the clock spring 66 to the cylindrical spring cover 94. With the parts assembled in the order shown in FIG. 7, the cylindrical cover 94 is secured within the cylindrical recess 90 in the housing 68 and to the plate 22 by a screw 102 and a nut 104. A spacer 109 is provided such that when screw 102 and nut 104 are tightened, plate 22, spool 92 and cover 94 are not pressed together so tightly as to prevent rotation of plate 22 with respect to member 68. Space is provided between facing surfaces of plate 22 and housing 68 such that the headed of rivets or screws passing through holes 24, 26, 28 and 30 in foot plates 20 and 22 do not engage the housing 68. Cylindrical projection 86 is provided with keys 105 on the outer surface thereof, which engages a corresponding notches 107 in the internal bore of spool 92, such that the plate 22 and spool 92 are keyed for rotation together.

Torque is applied between the housing 68 and the plate 22 by rotating the cylindrical cover 94 and therefor the outer end of the clock spring 66 until the desired amount of torque is applied therebetween. The cover 94 is held in the desired position by the engagement of a retaining mechanism including a detent 106, which is spring loaded by spring 108, with a selected one of a plurality of notches 110 in the cover 94. With the coil spring is installed as shown in FIG. 7, the spring will cause a torque to apply between the housing 68 and the plate 22 to cause the plate 22 to rotate in the direction as shown by the letter "A" with respect to the housing 68. If a corrective torque in the opposite direction is desired, the clock spring 66 would be removed and reinstalled so that it is wound in the opposite direction. A latch member 112 is provided for releasing the plate 22 from the housing 68. Applying an inward face on latch member 112, pushes keys 105 inwardly such that it is disengaged from the notch in the internal bore of spool 92, thus permitting separation of plate 22 from housing 68.

As was the case in the first embodiment, the torque to be applied to the limbs of the user can be adjusted by selecting the appropriate notch 110 in the cover 94 to be engaged by the detent 106 which is received in cavity or slot 111 in housing 68. Further, different springs can be used so as to provide more or less torque. Further, it is envisioned that the torque applying assembly as shown in FIG. 7 can be provided on only one of the plates 20 or 22, or on both of them.

Figure 8:
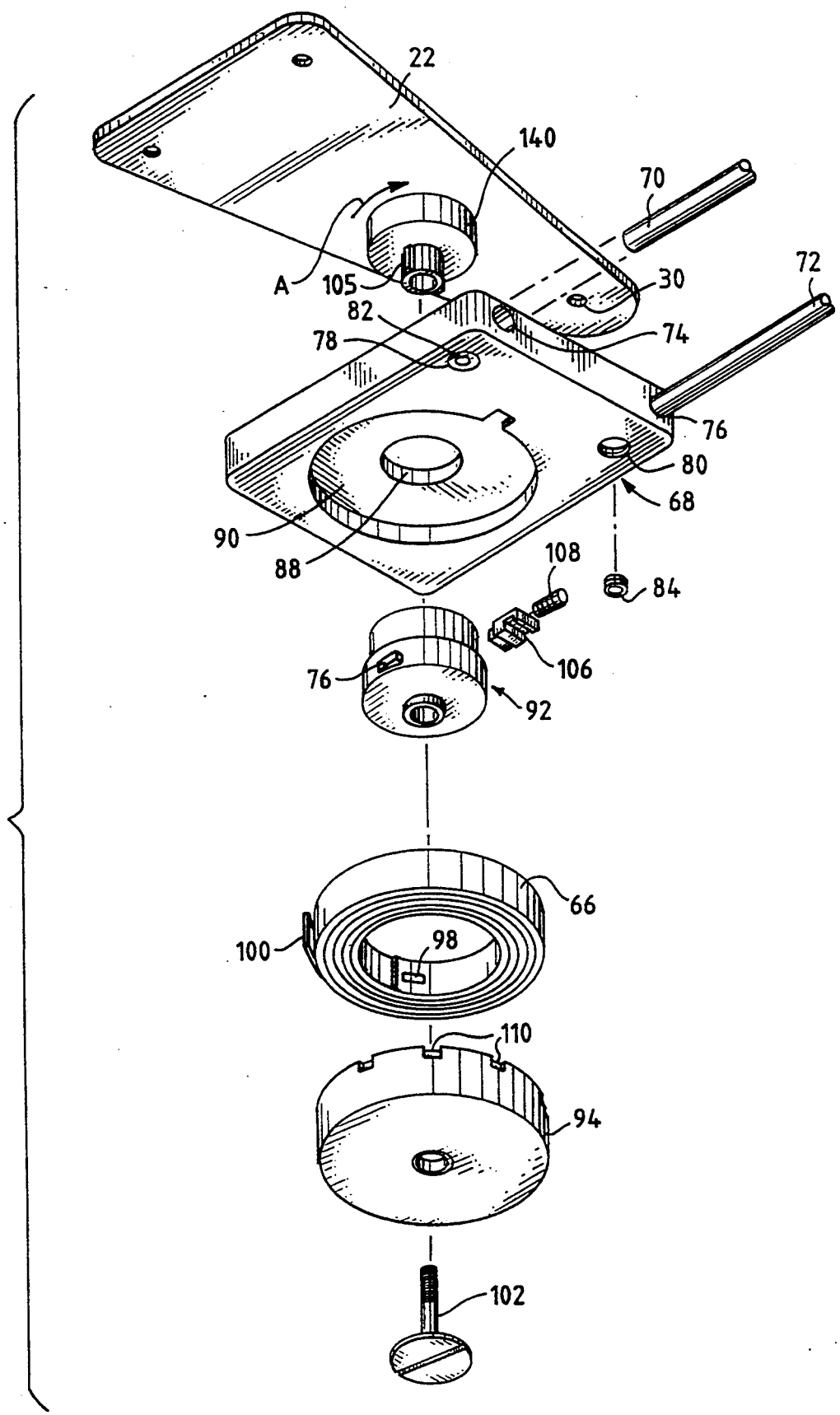
FIG. 8 is an exploded view of a portion of a third embodiment of this invention.

A third embodiment of this invention is shown in FIG. 8. This embodiment is similar to that shown in FIGS. 5, 6 and 7, and closely corresponds in the details shown to FIG. 7. Like components in FIG. 8 are identified by the same numerals as used in FIG. 7. One of the principal differences between the embodiment shown in FIG. 8 and that shown in FIG. 7 is in projection 86 being formed with a spacer 140 to provide clearance between facing surfaces of foot plate 22 and housing 68 for the heads of fasteners used to secure the foot plate 22 to a shoe. Another difference is in the form of keys 105 which engage notches in the internal bore of spool 92.

The mode of operation of third embodiment shown in FIG. 8 is the same as that of the first embodiment shown in FIGS. 1, 5, 6 and 7.

Figure 9:
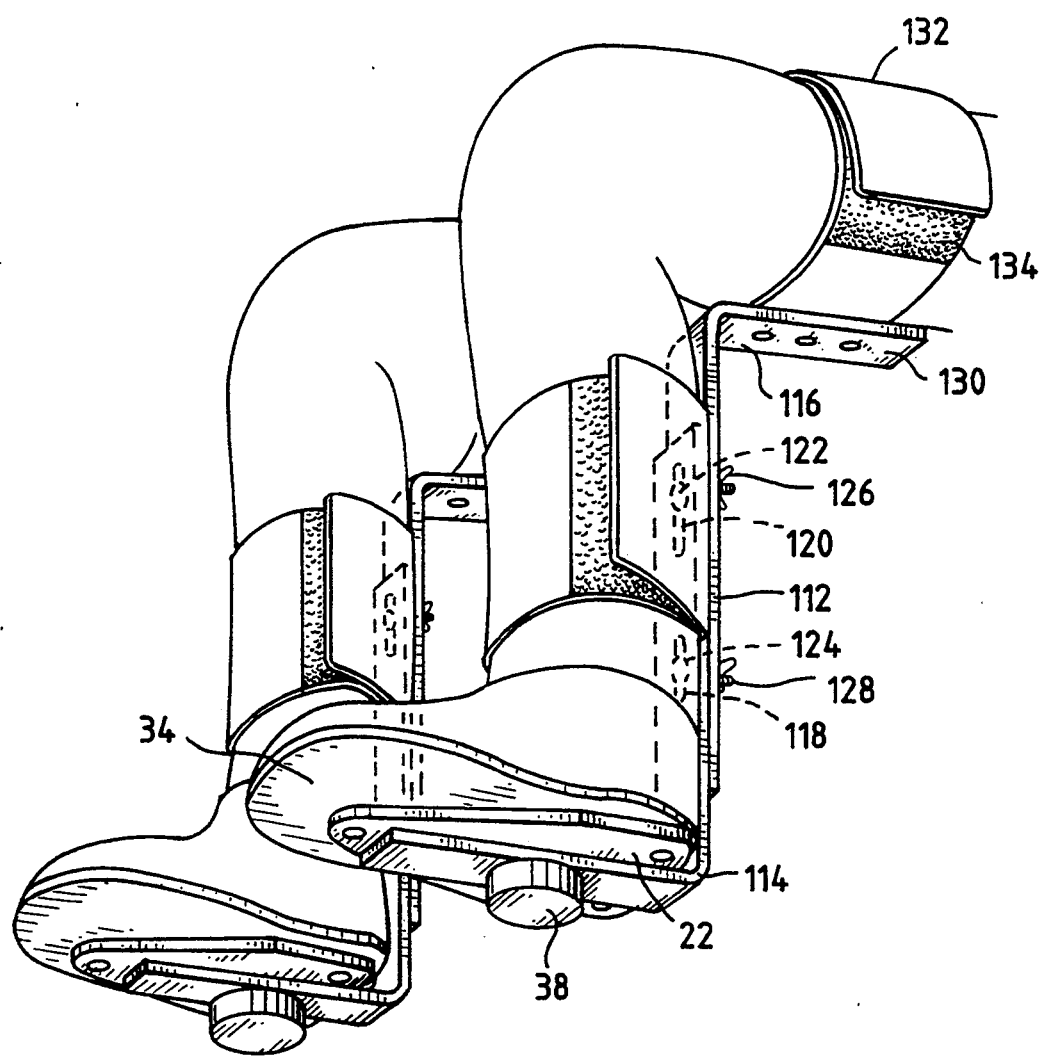
FIG. 9 is a perspective view of another application of the second embodiment of this invention.

Referring to FIG. 9, still another manner of applying the principles of the orthopedic appliance of the applicant's invention is shown. As shown in FIG. 9, the orthopedic appliance of this invention is adapted to apply a dynamic force to the lower extremity of a patient's leg without the need for an elongated spacing member or bar 'tying the feet together. As shown in FIG. 9, an adjustable Z-shaped assembly is formed from two L-shaped members 114 and 116. Holes (not shown) are formed in the one leg of the L-shaped member 116 while slots 118 and 120 are formed in the leg of the other L-shaped member 114. Fastening members which are shown as bolts 122 and 124 and wing nuts 126 and 128 are provided such that the overlap of the legs of the L-shaped members 114 and 116 can be adjusted to make the middle portion of the Z-shaped member 112 the appropriate length. The end portion 130 of the L-shaped member 116 is secured by a strap 132, which is shown as provided with inter-locking fastening means 134, to the upper leg of the patient. Similarly, the middle portion of the Z-shaped member 112 is secured to the lower portion of the leg by a strap 136, which is also shown as provided with a inter-locking fastening means 138.

Using the same numerals as set forth in FIG. 1, for similar components, the torque applying member 22 secured to the sole 34 of a shoe is pivotally supported on the lower end portion of the Z-shaped assembly 112 by a pivotal support mechanism 38. The pivotal support mechanism 38 contains a torque applying assembly 40 which applies a torque between the lower end portion of the Z-shaped assembly 112 and the torque applying member 22. In applying the applicant's orthopedic appliance in the manner of FIG. 9, either of the torque generating means as shown in FIGS. 2 through 4, or in FIGS. 5-7, may be used.

It should be apparent to those skilled in the art that while what has been described are considered at present to be the preferred embodiments of the orthopedic appliance of this invention, in accordance with the patent statutes, changes may be made in the orthopedic appliance without actually departing from the true spirit and scope of this invention.

The appended claims are intended to cover all such changes and modifications which fall in the true spirit and scope of this invention.

I claim:

1. An orthopedic appliance for applying a dynamic corrective torque to the extremity of a user so as to apply a corrective torque to the long bone of the user, said orthopedic device comprising,
   A. a Z-shaped member having a middle portion and first and second end portions, said end portions being generally perpendicular to said middle portion and extending in opposite directions from said middle portion,
   B. said first end portion being located behind and secured to the users leg above the knee,
   C. said middle portion being located behind and extending from the users knee to the bottom of the users foot,
   D. holding means for holding said middle portion behind the lower portion of the users leg, E. said second end portion being located under the foot of the user, F. a torque applying member supported for rotation on said second end portion, G. an attachment means for securing the foot of the user to said torque applying member for rotation therewith, H. a torque generating means, I. a means for supporting said torque generating means to apply a torque between said second end portion and said torque applying member whereby a dynamic torque is continuously applied to the long bone of a user.

2. The orthopedic appliance of claim 1, wherein said torque generating means is a coil spring.

3. The orthopedic appliance of claim 2, wherein said coil spring is formed of round spring wire.

4. The orthopedic appliance of claim 3, wherein said coil spring has a first and a second end, said first end of said coil spring being anchored on said second end portion, and the second end of said coil spring being anchored on said torque applying member.

5. The orthopedic appliance of claim 4, wherein two or more anchor means are provided on said second end portion for said coil spring, preselecting the torque applied to said torque applying member by preselecting one of said anchor means for anchoring said first end of said coil spring.

6. The orthopedic appliance of claim 4, wherein two or more anchor means are provided on said torque applying member for said coil spring, preselecting the torque applied to said torque applying member by preselecting one of said anchor means for anchoring said second end of said coil spring.

7. The orthopedic appliance of claim 5, wherein said anchor means are projections extending from said second end portion which are engaged by said coil spring.

8. The orthopedic appliance of claim 5, wherein said anchor means are projections extending from said torque applying member which are engaged by said coil spring.

9. The orthopedic appliance of claim 4, wherein two or more first anchor means are provided on said second end portion for said coil spring, and two or more second anchor means are provided on said torque applying member for said coil spring, preselecting the torque applied to said torque applying member by preselecting one of said first anchor means for anchoring said first end of said coil spring and by preselecting one of said second anchor means for anchoring said second end of said coil spring.

10. The orthopedic appliance of claim 3, wherein said torque applying member is supported for rotation on said second end portion by a pivot pin, and said coil spring is coiled around said pivot pin.

11. The orthopedic appliance of claim 2, wherein said coil spring has inner and outer ends and is formed from an elongated strip of flat spring material.

12. The orthopedic appliance of claim 11, wherein a housing is provided for receiving said coil spring.

13. The orthopedic appliance of claim 11, wherein said torque applying member is supported for rotation on said second end portion by a pivot means.

14. The orthopedic appliance of claim 13, wherein said pivot means includes a pin secured to and projecting from said torque applying member.

15. The orthopedic appliance of claim 14, wherein an inner anchor means is provided to anchor said inner end of said spring to said pin, and an outer anchor means is provided to anchor said outer end of said spring to said second end portion.

16. The orthopedic appliance of claim 11, wherein a tension adjusting means is provided to adjust the torque applied by said coil spring to said torque applying member.

17. The orthopedic appliance of claim 16, wherein said spring is wound around a spool, with said inner end of said spring being anchored to said spool, said spool being keyed to said pin, a pocket being provided in said second end portion, a spring cover being received in said first and second pockets, said outer end of said spring being anchored to said spring cover, and said spring cover being adjustably secured to said second end portion so as to provide for adjustment of the torque applied by said spring to said torque applying member.

* * * * *